United States Patent
Harel et al.

(10) Patent No.: US 7,311,107 B2
(45) Date of Patent: Dec. 25, 2007

(54) NAVIGATING AND MANEUVERING OF AN IN VIVO VEHICLE BY EXTRACORPOREAL DEVICES

(75) Inventors: Alex Harel, Savyon (IL); Uzi Dan, Ganei Yehuda (IL); Ehud Katzenelson, Ramat Yishai (IL); Zvi Raviv, Gan-Ner (IL)

(73) Assignee: BBMS Ltd., Savyon (IL)

( * ) Notice: Subject to any disclaimer, the term of this patent is extended or adjusted under 35 U.S.C. 154(b) by 751 days.

(21) Appl. No.: 10/686,535

(22) Filed: Oct. 16, 2003

(65) Prior Publication Data

US 2004/0138552 A1 Jul. 15, 2004

Related U.S. Application Data

(63) Continuation-in-part of application No. PCT/IL02/00286, filed on Apr. 8, 2002.
(60) Provisional application No. 60/331,559, filed on Nov. 19, 2001.

(30) Foreign Application Priority Data

Apr. 18, 2001 (IL) .................................. 142682

(51) Int. Cl.
*A61B 19/00* (2006.01)
(52) U.S. Cl. ..................................... 128/899
(58) Field of Classification Search ............. 128/653.1, 128/897–899; 600/9, 11–14, 102, 103, 109, 600/114, 117, 160, 166; 604/95; 364/413.13, 364/413.14; 606/130
See application file for complete search history.

(56) References Cited

U.S. PATENT DOCUMENTS

| | | | |
|---|---|---|---|
| 4,278,077 A | | 7/1981 | Mizumoto |
| 4,689,591 A | * | 8/1987 | McDougall .................. 335/299 |
| 5,217,449 A | | 6/1993 | Yuda et al. |
| 5,558,091 A | | 9/1996 | Acker et al. |
| 5,604,531 A | | 2/1997 | Iddan et al. |
| 5,638,819 A | | 6/1997 | Manwaring et al. |
| 5,681,260 A | | 10/1997 | Ueda et al. |
| 6,083,163 A | * | 7/2000 | Wegner et al. .............. 600/429 |
| 6,240,312 B1 | | 5/2001 | Alfano et al. |
| 6,950,689 B1 | * | 9/2005 | Willis et al. ................. 600/407 |
| 2001/0051766 A1 | * | 12/2001 | Gazdzinski .................. 600/309 |

FOREIGN PATENT DOCUMENTS

| | | |
|---|---|---|
| DE | 4313843 | 11/1994 |
| EP | 0667115 | 8/1995 |
| WO | WO99/18852 | 4/1999 |

* cited by examiner

*Primary Examiner*—Samuel G Gilbert

(57) ABSTRACT

A device for mobilizing, rotating and maneuvering an in vivo vehicle introduced into a subject by extracorporeal devices which control the position and motion of such a vehicle by detection and modulation of the strength and direction of the electromagnetic field vector of the vehicle. This invention employs a series of pulses, with specific characteristics over time, to induce magnetic field changes. The changes that result from the vehicle movement are measured and used to calculate the location and movement of the vehicle. A system and method for controlling the movement of the vehicle are also provided.

72 Claims, 17 Drawing Sheets

200 →

202

204

210 →

212

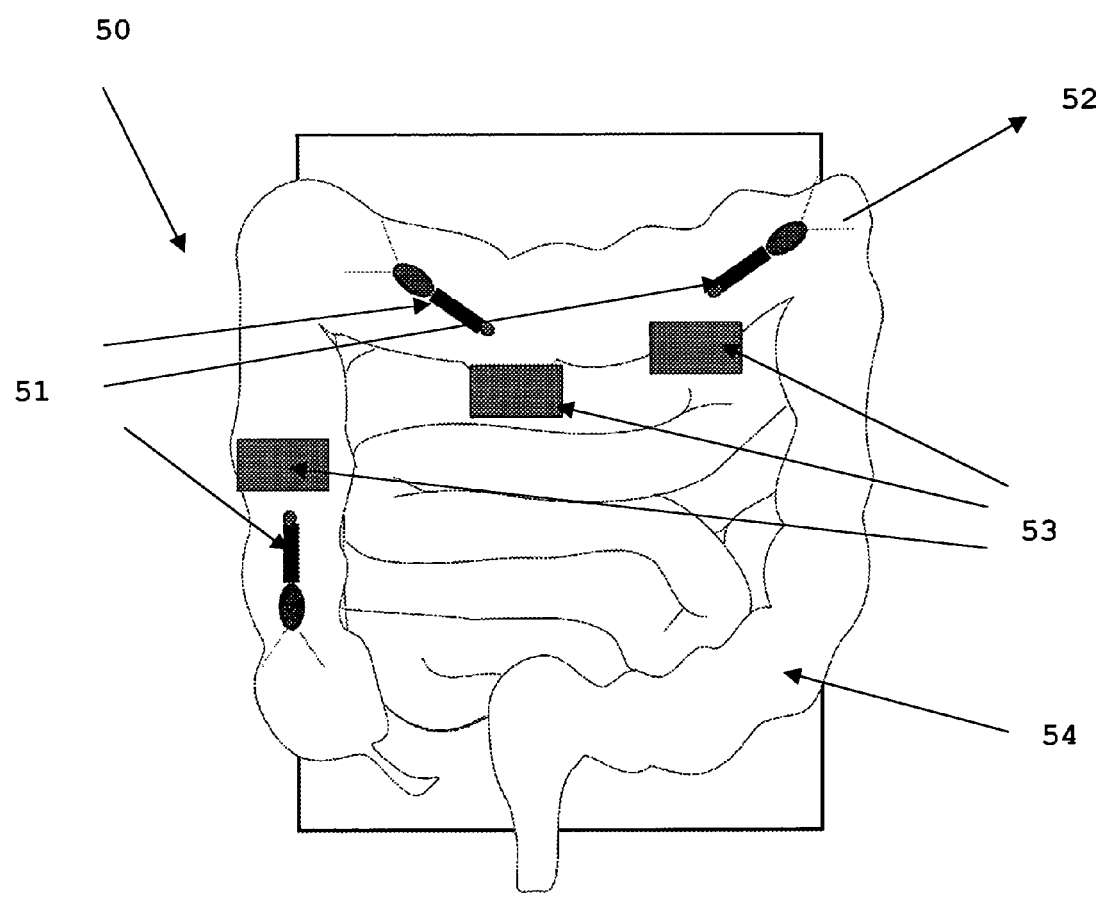

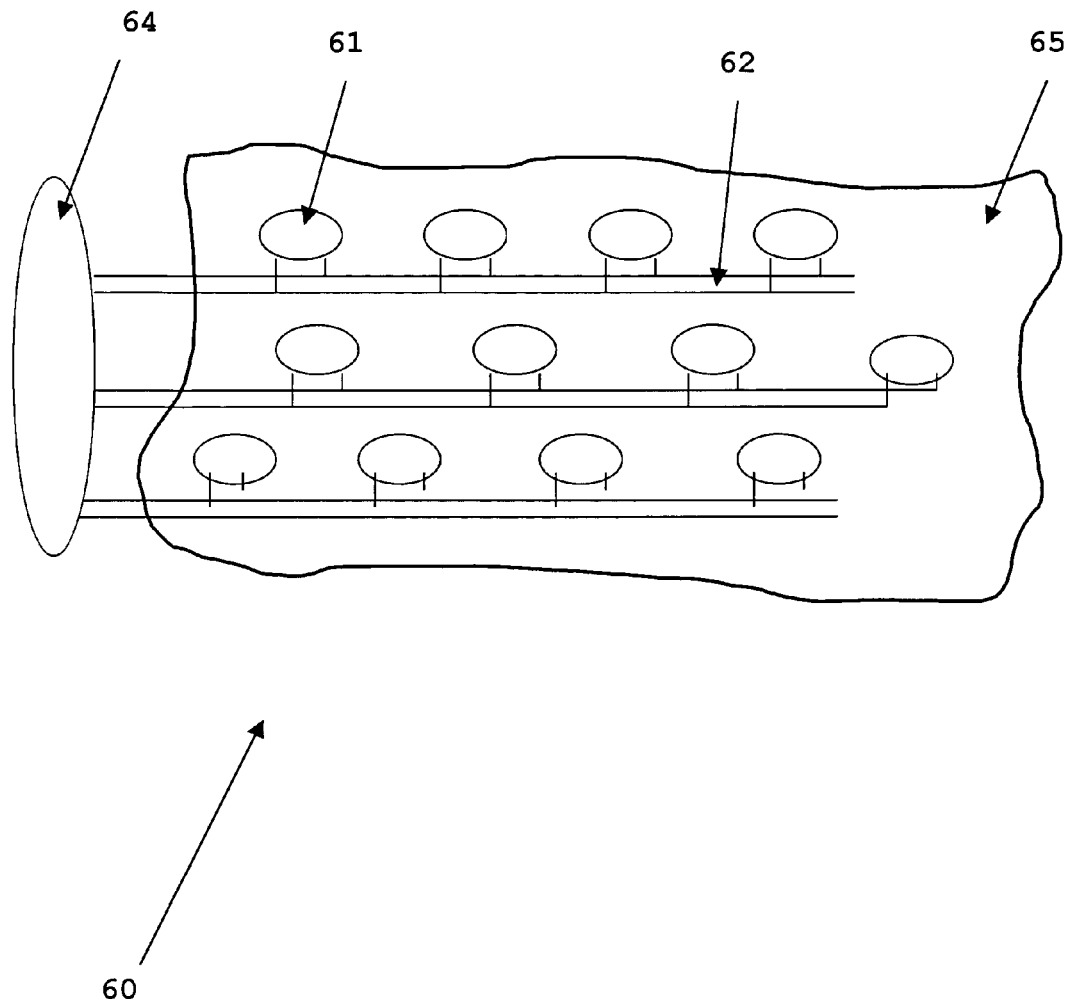

NAVIGATING AND MANEUVERING OF AN IN VIVO VEHICLE BY EXTRACORPOREAL DEVICES

This is a continuation-in-part of PCT Application No. PCT/IL02/00286, filed Apr. 8, 2002, currently pending, which claims priority from U.S. Provisional Application No. 60/331,559, filed Nov. 19, 2001, and Israel Patent Application No. 142682, filed Apr. 18, 2001, all of which are hereby incorporated by reference as if fully set forth herein.

FIELD OF THE INVENTION

The present invention relates to a device and system for mobilizing, rotating and maneuvering of an in vivo vehicle by extracorporeal devices, and in particular to mobilizing, and controlling the movement of an in vivo vehicle by remote activation of force and moment of magnetic or electric fields.

BACKGROUND OF THE INVENTION

High resolution imaging of lumens and epithelial surfaces of internal organs is required for many different types of diagnostic procedures. Among imaging techniques employed in modern medical practice are X-ray, ultrasound (US), magnetic resonance imaging (MRI), computerized tomography (CT) and positron emission tomography (PET). These methods rely on measuring and recording physical parameters of internal body parts, and transforming these parameters into informative images. These methods require expensive equipment, not all of which is available in many small and medium size medical centers (especially MRI). These diagnostic procedures also require several skilled practitioners (doctors, nurses and operators) to perform the procedure and interpret the image outputs. All of these factors together lead to relatively high costs of such procedures to the medical health insurance system, while their frequency of use is increasing.

Direct visual observation of internal body organs, like blood vessels, the gastrointestinal tract (GI), lungs, pelvis and abdomen, have significant advantages over indirect diagnostic imaging mainly because it allows real time observation, and the possibility of obtaining a sample for histological examination. The most common method of directly examining the upper or lower GI tract, as well as for examining other body cavities, is endoscopy. The physician has a real time image (either directly or via an external monitor) of the surface or lumen under investigation. The picture recorded in the endoscopic procedure is produced by optical and electro-optical instruments that are inserted into the body in the form of a long, semiflexible tube. One disadvantage of endoscopy and similar methods is the requirement of a direct connection (rigid or flexible) from the examined area to the detector system outside of the body. Another disadvantage is that the instrument does not move easily through the body cavities, causing discomfort to the patient and putting him at risk for complications such as bleeding and infection, accompanied by significant inconvenience.

An alternative to endoscopy is a method which employs a wireless vehicle inside the body capable of gathering and transmitting image data to outside the body. Such a method is taught by U.S. Pat. Nos. 4,278,077, 5,217,449, 5,604,531, and 6,240,312 which describe in vivo camera systems for examination of internal body lumens. Such an imaging and transmitting device can be any in vivo vehicle that can transmit information outside the body. The movement of such devices depends on external direct aiming (via endoscope or catheter), or, more commonly, on natural movement such as blood flow or peristaltic motion of the digestive muscles.

Relying on peristaltic bowel movement has an inherent disadvantage. When the vehicle is in the colon, the peristaltic movement occurs only if the colon is filled with some fecal content. However, when the colon is filled or partially filled with feces, the observation capability is dramatically reduced. Emptying the colon before inserting the vehicle significantly reduces the peristaltic bowel movement, therefore limiting the vehicle movement. In addition, relying only on the peristaltic movement restricts the area under observation, especially in large spaces such as the stomach and colon.

Another significant disadvantage of a passively driven in vivo video device is the fact that the capsule is constantly transmitting pictures for as long as it is in the body, even when it is not needed. Such continuous operation is inefficient and consumes a lot of energy.

Furthermore, passive devices have the disadvantage of the lack of control over the movement and general behavior of the device within the body. An external operator cannot easily control such movement, nor can the operator easily manage the behavior of the device within the body. Therefore, the device may enter an undesirable location, and/or otherwise behave in a less than optimal manner for the type of diagnostic procedure which is being performed.

SUMMARY OF THE INVENTION

The background art does not teach or suggest a device or system for actively controlling the movement of an in vivo vehicle introduced into a subject. The background art also does not teach or suggest such control which is based on changes in the magnetic field or electric field vectors produced by an external electromagnetic source, by extracorporeal devices equipped with electromagnetic sources or both of these types of control. The background art also does not teach or suggest a system or method for controlling an in vivo vehicle via changes in the magnetic or electric field vectors from outside of the body, without a direct mechanical or physical connection to the vehicle. Lastly, the background art does not teach or suggest an algorithm for estimating the position and orientation of the vehicle. The background art also does not teach or suggest that combinations of force and field measurements can be used to calculate the vehicle position and orientation.

The present invention overcomes these deficiencies of the background art by providing a device and a system for mobilizing, rotating and maneuvering an in vivo vehicle introduced into a subject by extracorporeal devices which control the position and motion of such a vehicle by detection and modulation of the magnitude and direction of magnetic field vector of the vehicle. This invention preferably induces magnetic field changes with specific characteristics over time. The changes that result from the vehicle movement are measured and used to calculate the location and/or movement and/or orientation of the vehicle.

One exemplary embodiment of the present invention is to use one or more pulses in the electromagnetic field (if used) to induce magnetic field changes. These pulse(s) preferably are time dependent, for calculating the location and/or movement of the vehicle. Since the response of the magnetic material of the vehicle to these pulse(s) is linear according to the activating pulse(s), and therefore has the same time dependence, the signal can be separated from the noise for locating the vehicle.

Preferably, the present invention provides a device and a system for mobilizing, rotating and maneuvering an in vivo vehicle by remote activation of force and moment of applied magnetic or electromagnetic fields. Application of force and moment on the magnet (or material that is magnetized or magnetizable) which is associated with the vehicle enables remote control of the vehicle's movement along all axes and all rotations around any given axis.

It is therefore provided, in accordance with a preferred embodiment of the present invention, a vehicle which is introduced into a luminary space of the body and which consists of an element that may be controlled by a controlling device outside of the body. The vehicle can also travel passively through the body lumen via peristaltic motion.

Additionally, the present invention discloses the use of an external magnetic or electromagnetic field for activation, generation of electrical force, electromotive force (emf) and magnetic flux changes which move, rotate, monitor and direct the magnet-containing vehicle in different directions in order to perform various kinds of tasks as described herein below.

In accordance with another preferred embodiment of the invention, the magnetic system of the in vivo vehicle may optionally and preferably be implemented according to one of the following configurations: as an integral part of the original vehicle; as an integral part of the original vehicle, but upon introduction into the subject, the magnet is released from the vehicle as a tethered object to the vehicle, in which the connecting element between the vehicle and the magnet can again optionally serve as an antenna; and as at least a partial exterior coating of the vehicle.

The magnetic system of the vehicle may optionally feature sintering magnetic material or bonded material. This bonded magnetic material may optionally compose part of a biodegradable container, magnetic powder or magnetic particles, which dissolve(s) with time, thereby allowing the removal of the magnetic substance from the body. For this configuration, the bond is preferably dissolvable, dispersible or otherwise soluble in an aqueous solution. After dissolving, the magnetic material is preferably in a powder form. The attractive force of the individual particles of powder is very low and they can move freely, thereby being capable of changing geometric dimensions according to the dimensions of the surrounding structure.

In the configuration where the magnetic material covers all or part of the outer surface of the vehicle and the internal structure of the vehicle is protected by a layer of ferromagnetic material, then a magnetic field inside the vehicle is preferably not produced; this feature protects the internal sub-systems of the vehicle.

Moreover, in accordance with another preferred embodiment of the invention, one or more capacitors can be installed into the body of the vehicle, which can be charged by an internal battery. In this embodiment, movement of the vehicle is achieved by applying an electric field on the electric charge of the capacitor(s). This may be accomplished with or without a permanent magnet in the extracorporeal controlling unit.

Additionally, the present invention also relates to the combination between an external magnetic field and an internal permanent magnet integrated into the vehicle which would enable, in addition to the guidance and monitoring of the vehicle, other uses such as: measurement of the vehicle's location (via a tracking system) by calculating the changes in magnitude and orientation of the magnetic field vector produced by the in vivo vehicle, and the changes in the force exerted on the coils of the tracking system (if present); and performing triggering actions such as activating and/or initializing and/or shutting down activities of the vehicle's systems, in which the triggering activities may optionally be based on vehicle location or on any other meaningful parameter during the diagnostic procedure.

One advantage of the present invention is its ability to control the direction and speed of the vehicle in large spaces, i.e. the stomach, small intestine, colon and other abdominal as well as pelvic spaces. In addition, by employing the present invention, it is possible to accurately control the position of the vehicle in an empty space, thus enabling a clear field of observation of the lumen and surfaces. The present invention also enables the guidance of one or more vehicles to a specific anatomical area when a more focused observation is required.

In another preferred embodiment of the invention, the vehicle is able to report its position while inside the subject and can be easily detected upon passing a particular location in the body of the subject (patient), for example when exiting the body of the subject. This embodiment may optionally be implemented with at least one reed switch, which is a device that is sensitive to magnetic fields, and transmits a signal upon sensing such a field. When the reed switch becomes activated, the vehicle is near that switch, such that if the reed switch is optionally placed near the location of interest, the vehicle can optionally be detected as it passes that location (for example, as it exits the body).

Additionally, in another preferred embodiment of the invention, the system includes an array of reed switches that map the body or a portion thereof, thereby define the location of the vehicle in the body. A two-dimensional array of such switches may optionally be placed on (adjacent but external to) the patient's body. As the vehicle moves through the body, certain reed switches are activated. The geometrical center of the activated switches represents the position of the vehicle.

Moreover, in another preferred embodiment of the invention, during the use of the vehicle, energy can be saved, thus reducing the power consumption. The power saving can reduce the volume of the energy source needed in the vehicle, leaving more volume for other elements. Timing of vehicle functions can optionally be accomplished by one or more of: time measurement; measuring the change in the pH and/or the concentration of electrolytes in the vehicle's immediate environment; pressure changes in the vehicle's immediate environment (i.e. the muscle of the ileo-cecal valve, local pressure changes, and so forth); and through an outside element, such as a reed switch for example. Pressure changes may optionally be measured through a pressure sensitive capacitor or resistor, for example.

In accordance with another preferred embodiment of the invention, other functions can be included in the repertoire of the vehicle's utilities. These functions may optionally include one or more of: histology and sampling; fluid concentration sampling; local surgical procedures; and drug delivery. These functions are optionally and more preferably performed by activation of the function in the vehicle, most preferably through the external control system of the present invention (as described in greater detail below), which would in turn activate some type of mechanical, electronic, electrical, optical, or chemical component(s) or combination thereof to perform the function.

Finally, in another preferred embodiment of the invention, hard magnetic or ferromagnetic beads or particles can be coated with a pharmaceutical compound for concentrated delivery to a specific body part via the extracorporeal control system. This particulate drug delivery system could optionally be injected into the blood or into an appropriate location and concentrated in that location for optimal effect via detection and modulation of the magnetic field vectors of the magnetic particles.

It should be noted that although the following description is directed toward the use of the present invention in the GI tract, this is for the purposes of illustration only and is not intended to be limiting in any way, as the present invention is suitable for use in any bodily cavity, space, vessel, organ or other non-solid section of the body.

Hereinafter, the term "magnet" includes soft and hard magnets, magnetic material, material that is magnetized and material that is magnetizable.

Hereinafter, the phrase "managing the vehicle" includes at least one of maneuvering, locating, mobilizing, controlling, monitoring (the vehicle) and activating at least one vehicle function.

BRIEF DESCRIPTION OF THE DRAWINGS

FIG. 5 is a schematic diagram for depicting the system for controlling and maneuvering the vehicle in the subject's colon;

FIG. 6 is a schematic diagram for depicting the detection and motion control systems combined in a single element, showing that the field generator units may also optionally be used as detectors, while the field generating/detector units are preferably distributed on a flexible material and are preferably connected to the computerized control unit;

DETAILED DESCRIPTION OF THE INVENTION

Figure 1:
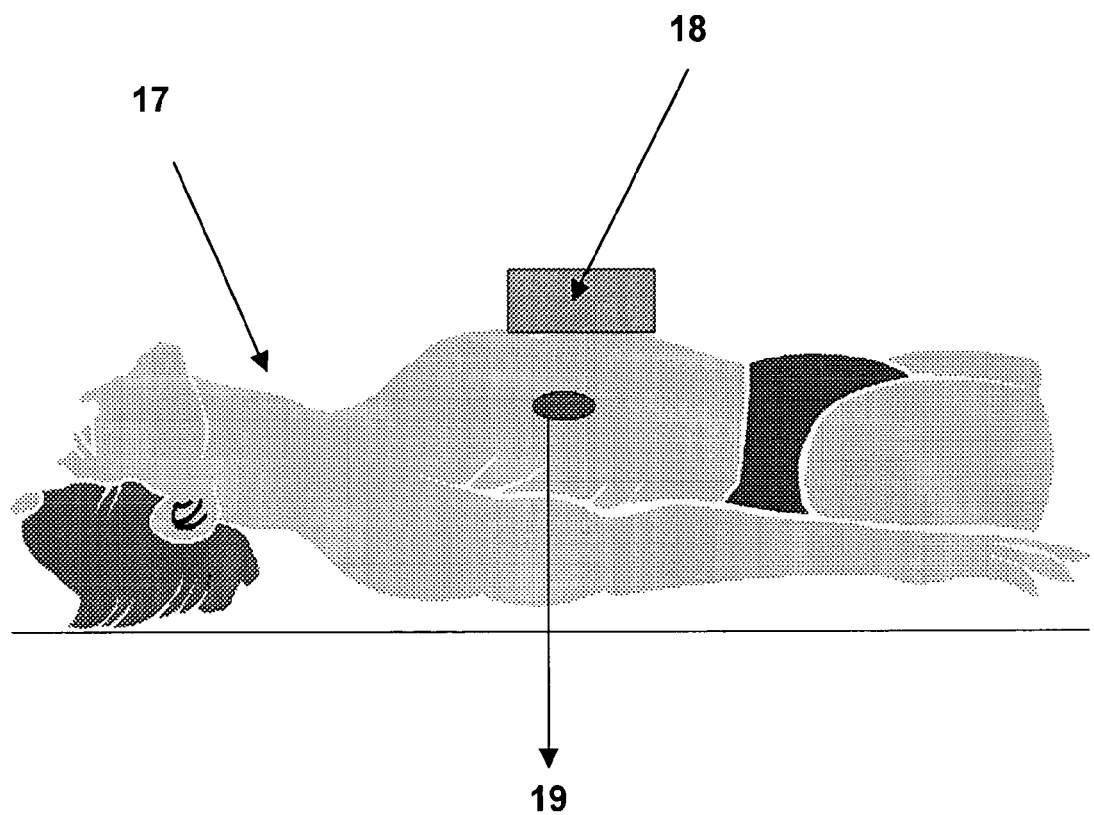
FIG. 1 is a general schematic diagram for depicting the elements of the system and their layout.

The present invention discloses a device and a system for mobilizing, rotating and maneuvering an in vivo vehicle introduced into a subject by extracorporeal devices. Preferably, the present invention provides a device and a system for mobilizing, rotating and maneuvering an in vivo vehicle by remote activation of force and moment of an applied magnetic or electromagnetic field.

A magnet, optionally made of any suitable biologically compatible magnetic, magnetized or magnetizable material, is installed inside or coats the outside of a vehicle, or is attached to it by a connecting element. If the magnet is located within a sealed portion of the vehicle or is otherwise sealed, then optionally the magnet may be constructed of a less biologically compatible, or even a biologically incompatible, material.

Preferably, if the magnet is constructed of an alloy, the magnetic alloy is composed of one or more of Neodymium-Boron-Iron (NdBFe), Samarium Cobalt (SmCo) or other similar compounds. The magnet can optionally be made of any hard or soft permanent magnetic (e.g. ferromagnetic) material that is magnetized under the influence of a magnetic or an electromagnetic field. The magnet's mass and physical properties include magnetization direction and magnitude that enable the movement, rotation and maneuvering of the vehicle.

For management of the vehicle, preferably including at least one of movement, rotation, activation of a function and/or other types of control of the vehicle in the body of the subject, an extracorporeal magnetic or electromagnetic field is preferably used. This magnetic source consists of a permanent magnet, an electromagnet or an electromagnet with soft magnetic material or any combination thereof.

In addition, the extracorporeal electromagnet may be composed of several coils that create a magnetic field or fields in various directions and with various gradients. In one configuration, each coil in the electromagnet can be operated separately. In another configuration, each group of coils in the electromagnet can optionally be operated synchronously and also separately. Different currents can feed each coil and/or each group of coils. Similarly, the force vector (magnitude and direction) applied on the external magnetic field source is measured, and used as feedback to control the status between the in vivo permanent magnet and the external magnetic field source. The same coils can optionally and preferably be used to calculate the vehicle's location.

The current density that can be achieved in a resistive coil is much smaller than the equivalent effective current density on the surface of the permanent magnet, as is explained in detail herein below. When having an extracorporeal magnet composed of several coils that create a magnetic field, a strong current density is required. Due to the abovementioned property of coils, there is a restriction on the current density that can be achieved. This restriction on the strength of the electrical current may restrict the ability to move or control the vehicle inside a body lumen.

As an example, consider that the current density in a straight, not coiled wire, is about 5 ampere/mm². The equation below demonstrates that a coiled wire has a lower current density.

$$F \propto I \sum_i \frac{4\pi\mu * \left(-3 * \frac{z_i}{a_i}\right)}{a_i^3 * \left(1 + \left(\frac{z_i}{a_i}\right)^2\right)^{2.5}} \quad \text{equation 1}$$

This equation represents the force calculation of a coil on the axis. The sum in the equation is over the number of full rounds in the coil. The symbol $a_i$ represents the distance of the center of the $i^{th}$ wire from the axis, and $z_i$ represents the distance of the $i^{th}$ wire from the object on which the force is acting. The symbol I represents the current in the wire forming the coil.

From the above equation one can see that the distance from the axis is measured in units of $a_i$. In a case where $z_i > a_i$ the above equation behaves like the function $a_i/z_i^4$ and decreases rapidly with the distance. Therefore, although increasing the radius of the coils will increase the force, the greater distance from the body will decrease it much more rapidly, and the force will not be strong enough. For example, for a coil of radius 5 mm, which has current density of less than 5 ampere/mm², the force created is practically limited to a height of 4 mm from the base of the coil.

Due to the limitation on the current density as described above, the small size of the coil means that there is a limitation on the force that the coil can impose on the vehicle. A small imposed force requires the vehicle to be in short distance from the coil matrix. A force amplifier is needed in order to enlarge the force a small coil can create.

The force amplification can be achieved in several ways:

An optional solution to the above mentioned problem is to use a matrix of coils, which can be activated and deactivated, and thus control the movement of the vehicle. The vehicle will move to the geometric center of the activated coils. In order to know the vehicle position with a good resolution, the coils composing the matrix must be of small dimension, namely having a size in the order of millimeters, and not centimeters. The size of the pixel (i.e. location discretization) is half of the coil diameter. If a localization is required within 1 cm, the coil size radius is limited to 1 cm, for example. Therefore, the discretization size determines the coil size. In other words the size of the coils determines the "pixel" size of the vehicle.

The matrix of coils can also be used in order to move a permanent magnet, which then moves to the center of the activated coils, and creates equivalent effective high current density at this point. The equivalent effective high current density then amplifies the force created by the coils on the vehicle.

Another possibility is to use a matrix of cylindrical permanent magnets arranged on a grid, instead of the coils matrix. Cylindrical magnets are chosen as they are the most efficient way to utilize the space, but the magnet can optionally be ring shaped, a polygon or a polygonal ring. The cylindrical magnets are magnetized in the axial direction. The formula for calculating the force created by the cylindrical magnets is the same as equation 1, only that the sum is performed only on the cylindrical surface. The idea behind the system is space discretization, which is achieved by dividing the surface to regions of the magnetic field. A surface pixel is defined by a region having magnetic field in the same direction, when all its nearest neighboring (non diagonal) pixels have a magnetic field in the opposite direction. In this way, each magnet has a magnetization opposite to the magnetization of its nearest neighbors.

On the movable permanent magnet, several coils are attached and are wound in opposite directions (at least one coil is wound clockwise and at least one other coil is wound counterclockwise). In this way, the electromagnetic fields caused by each pair of coils are in the same direction, and thus enhance each other. In addition, the pair of coils are mounted on ferromagnetic material, increasing the magnetic field, and thus also the force in the system, to an even greater extent.

When using the matrix of cylindrical magnets as described above, the movement of the vehicle in the body lumen is caused by a change in the direction of the current in the coils attach to the driving magnet. It is possible to add a third coil to each pair to break the symmetry of coils, making it possible to give preference to one of the pairs of coils, thus creating a preferred direction of movement.

In order for movement to start, a coil is added which is not placed below the magnet center. The added coil will experience non axial force, which will create a movement. Once the system moves, the force on the major coils will no longer be axial, and the added symmetry breaking coils can be shut down. In order to initiate movement, preferably the symmetry breaking coils are used, and in later stages preferably the inertia serves as a tool for breaking the symmetry in the system.

In one preferred embodiment of the present invention, several Hall-effect probes are added to monitor the movement of the force amplifier relative to the matrix of cylindrical magnets. A Hall effect probe makes use of the known phenomenon (discovered by E. H. Hall in the $19^{th}$ century), such that when an electric current flows through a conductor in a magnetic field, the magnetic field exerts a transverse force on the moving charge carriers. A buildup of charge at the sides of the conductor balances this magnetic influence, producing a measurable voltage between the two sides of the conductor, which is proportional to the magnetic field. The Hall-effect probe thus monitors magnetic field changes and can be used to trigger a change of the current in the coils, when they pass from pixel to pixel. It can also be used for counting the number of pixels that the system moves.

In order to create movement, the current direction in the coils pair changes every time the coils move a distance similar to the distance between two magnets in the matrix, as for example in a linear motor. The Hall-effect probe measures the field changes, and is used for changing the current in the coils.

The measurement and tracking functions of the extracorporeal navigating system may optionally and preferably be accomplished by: an electromagnet used for maneuvering the vehicle; a coil or more preferably a set of coils, capable of measuring magnetic field strength in a plurality of, but more preferably all, directions; Hall effect probes; a pressure measuring device; or a combination thereof, in which these elements are more preferably connected to a computerized control system.

As stated, a Hall effect probe measures the magnetic field strength. This probe changes the electrical potential on the device when exposed to a magnetic field.

The pressure-measuring device may optionally be implemented as follows. When an electrical current in a coil is exposed to a magnetic field, a force acts on the coil. The coil creates pressure on its physical support, which can be measured. Calibration of the system enables the pressure to be translated to a measurement of the magnetic field, which can then optionally and preferably be used to calculate the vehicle position, for example.

The principle feature of the invention is the ability, via detection and generation of magnetic field vectors, to guide and maneuver the vehicle by an extracorporeal control unit, without the requirement for a physical connection between the vehicle and the control unit. The extracorporeal guidance aiming may optionally be performed in one or more ways, for example by following a pre-determined and/or programmed route, according to the anatomical structure of the organ in which the vehicle is situated. In this option, the software program preferably receives feedback from the tracking system. The software program can optionally and preferably correct mistakes, can limit the force applied on the vehicle to avoid damage to the tissue, and more preferably may activate procedures to re-locate the vehicle if it gets lost.

Another option is to use real time guidance, performed by the operator, according to information received from the vehicle. Alternatively, real time guidance may optionally be performed according to information received from any other imaging system (X-rays, US, MRI, CT, etc), which can optionally be gathered before or during the diagnostic procedure involving the present invention, or any combination thereof.

The mode of external remote guidance and/or monitoring may also activate or enable other functions. The external remote guidance preferably enables the navigation of the vehicle in different directions in the observed area.

According to preferred embodiments of the present invention, the in vivo vehicle has one or more preferred but optional features which allow it to be moved, turned, diverted and aimed at any angle. The electromagnetic receiving/signaling system of the vehicle may be composed of an electric dipole element or a magnetic element which forms an integral part of the vehicle or may be a separate element tethered to the vehicle by a connecting element. In the integrated configuration, the magnetic element may be composed of a permanent magnetic ring or disk inserted into the vehicle, a permanent magnetic coating covering part or all of the exterior of the vehicle or a bonded magnetic material coating part or all of the vehicle's exterior. Alternatively, the magnetic element may be composed of ferromagnetic material which may coat part or the entirety of the vehicle's exterior. In addition, the magnetic element may be composed of a permanent magnet, bonded and/or ferromagnetic materials. The direction of the magnetic field of the magnetic element inside the vehicle may be axial, or parallel to the diameter (diametrical) in a case where the vehicle's geometry is round i.e. cylinder, disk, and/or ring shaped or a combination thereof.

In one tethered configuration, the magnetic element is connected to the vehicle upon introduction into the patient, but is released from the vehicle at a certain stage in the diagnostic procedure and remains connected to the vehicle. In another preferred tethered configuration, the tethered magnet is introduced into the patient as such.

The vehicle may also contain an electric circuit such that force can be applied to the vehicle through the electronic circuit when the vehicle is in a magnetic field. The electric circuit can be installed in the vehicle in place of the permanent magnet or in addition to it. Additionally, the vehicle may also contain capacitors which may be charged by a power source. The capacitor or capacitors can be installed in the vehicle in place of the permanent magnet or in addition to it.

According to other optional but preferred embodiments of the present invention, there is provided a method for detecting the location of the vehicle and more preferably for also controlling the movement of the vehicle. First, a matrix of detectors are attached to the patient or placed close to the patient. The matrix can be composed of Hall effect probes, coils which serve as probes or combinations of these elements. For example, the magnetic field may optionally be measured with a Hall effect probe, as previously described. Alternatively, the field may optionally be measured according to the force acting on a coil when current flows through it, or alternatively by measuring the potential on a coil when a time dependent magnetic field is applied to it. This measurement enables the magnetic field caused by the vehicle to be calculated, such that the position of the vehicle can be calculated.

The probe detects at least one directional component of the magnetic field at any point of the matrix but may also be able to detect up to three directional components of the magnetic field. For a matrix composed of Hall effect probes, it is possible to detect both time dependent and stationary magnetic fields. For a matrix composed of coils, only a time dependent field can be detected directly, while the stationary field can be calculated from the force measurements.

For locating the vehicle, five parameters should preferably be calculated, namely three coordinates with respect to the detector matrix center and two orientation angles of the magnetization with respect to coordinate system defined on the detection matrix. At least five measurements of the magnetic field of the vehicle are needed to extract these parameters providing that the distance and the orientation of detectors within the matrix and the magnitude and the direction of the magnetization vector with respect to the vehicle are known. The extraction of the five parameters is done by best fit of the known formula of the magnetic filed at a point of distance ($d_x$, $d_y$, $d_z$) from a magnetic dipole.

For example: Let ($x_m, y_m, z_m$) be a position vector of a detector m in a coordinate system in which center of the matrix is in the origin; (x,y,z) be the position vector of the vehicle in the same coordinate system; and $R_m$ be the Euclidian distance of the vehicle from detector m. Therefore, $$R_m = \sqrt{(x_m-x)^2 + (y_m-y)^2 + (z_m-z)^2} \qquad \text{equation 2}$$

Denoting the z component of the vehicle's magnetization by $m_z$ the x, y, z components of the magnetic field at the point m are, respectively $$B_x^m = \frac{3m_z(x_m - x)(z_m - z)}{R_m^5} \qquad \text{equation 3}$$

$$B_y^m = \frac{3m_z(y_m - y)(z_m - z)}{R_m^5} \qquad \text{equation 4}$$

$$B_z^m = \frac{3m_z[(z_m - z)^2 + R_m^2]}{R_m^5} \qquad \text{equation 5}$$

Similar equations for $m_y$, and $m_x$ can be written by changing z to y and z to x in the above equations.

The unknown parameters are x, y, z, $m_z$ and $m_y$; the measured quantities are $B_x^m$, $B_y^m$, $B_z^m$. Using a best fit algorithm the best estimation of x, y, z, $m_z$, $m_y$, and $m_x$ and the error in the estimated value are then calculated. Then from the knowledge of the magnetization of the vehicle consistency can be checked i.e.

$$M=\sqrt{m_z^2+m_y^2+m_x^2} \quad \text{equation 6}$$

M is the measured vehicle magnetization.

When a force measurement is used (coil detectors), the relation between the known current in the m coil, $I_m$, the measured force, $F_m$ and the unknown magnetic field, is given by the Lorenz law, and realized by the following vector equation:

$$\vec{F}_m = \oint I_m \vec{ds} \times \vec{B} \quad \text{equation 7}$$

where the ds integral is performed along the coil. The current in the coil may change from coil to coil in the matrix to get the best measurement. Then a best-fit algorithm is used to estimate position and orientation of the vehicle from equation 7. Combinations of force and field measurement can be used to calculate the vehicle position and orientation. In the preferred embodiment the number of measurements is larger then the number of unknowns, as this should reduce the error. Minimally, at least as many measurements as unknowns are required for the calculation.

Reference is now made to FIG. 1 which illustrates the major elements of the system and their layout including an extracorporeal navigation system 18 for guiding an in vivo vehicle 19 within the patient 17. As shown, extracorporeal navigation system 18 is optionally in direct physical contact with at least a portion of patient 17 although this is not necessary, as physical proximity is sufficient. For example, vehicle 19 could optionally be used for diagnostic imaging techniques and/or other medical procedures.

Figure 2:
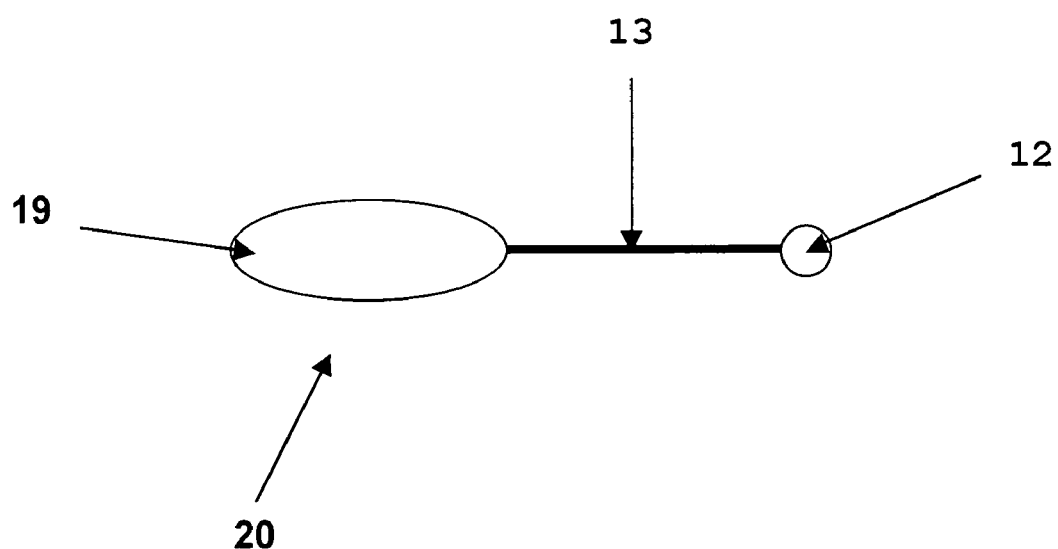
FIG. 2 is a schematic diagram for depicting the vehicle's magnetic system connected to the vehicle by a connecting element.

Reference is now made to FIG. 2 which depicts the tethered magnetic element configuration 20 of the vehicle where a separate magnetic element 12 is tethered to vehicle 19 by a connecting element 13. It should be noted, for the purposes of description for these drawings, that the term "magnetic element" includes any type of magnet, which as previously described may include one or more of a magnet (whether soft or hard), magnetized material or magnetizable material, or a combination thereof. Connecting element 13 is an exemplary tether for magnetic element 12, which is preferably flexible but alternatively is rigid. Connecting element 13 and vehicle 19 may optionally be constructed of a metal, an alloy, a plastic or a combination of materials, but may not necessarily be constructed of the same or similar materials. Connecting element 13 and/or vehicle 19 may optionally be from hundreds of microns to a few millimeters in length, although it should be noted that size is not necessarily a limiting factor. Rather, the dimensions of connecting element 13 and/or vehicle 19 are optionally and preferably chosen according to the dimensions of the body space or spaces in which vehicle 19 travels.

Magnetic element 12 may optionally be smaller than vehicle 19. One advantage of this embodiment is that magnetic element 12 does not need to fit within vehicle 19, such that a larger size of magnetic element 12 may optionally be used.

Figure 3:
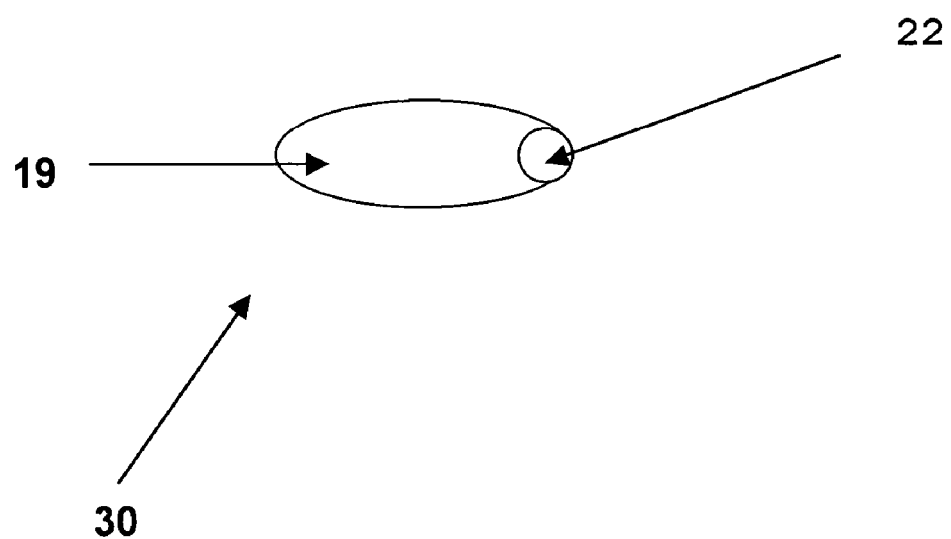
FIG. 3 is a schematic diagram for depicting the vehicle's magnetic system inside the vehicle.

Reference is now made to FIG. 3 which depicts an integrated vehicle configuration 30, where a magnetic element 22 is integrated into the body of vehicle 19.

Reference is now made to FIGS. 4a-4f, in which several types of vehicles are shown. It should be noted that the same reference numbers denote the same or similar elements.

Figure 4A:
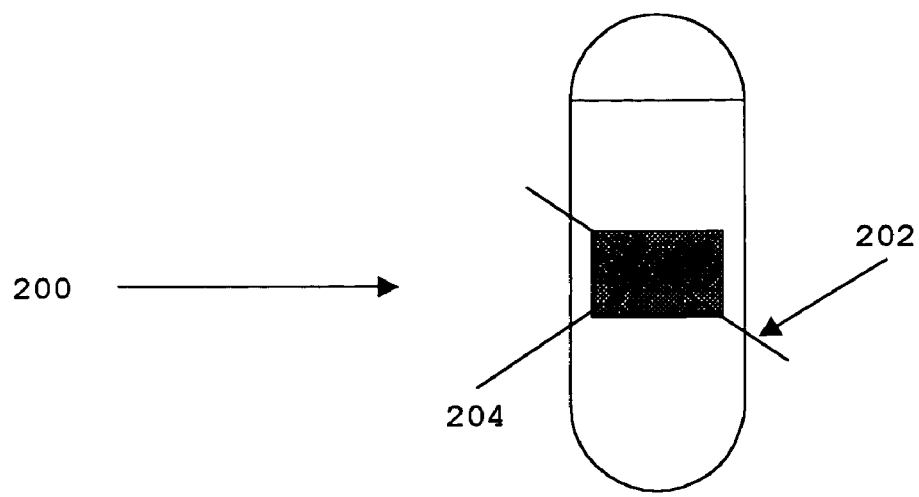
FIGS. 4A-G are schematic diagrams for depicting several possible configurations of the vehicle's magnetic system inside the vehicle or coating the outer surface of the vehicle.

As shown in FIG. 4a, a vehicle 200 preferably features an inserted magnet 204, optionally in the form of a ring or disk, which is more preferably permanently installed. A magnetization direction 202 is shown.

Figure 4B:
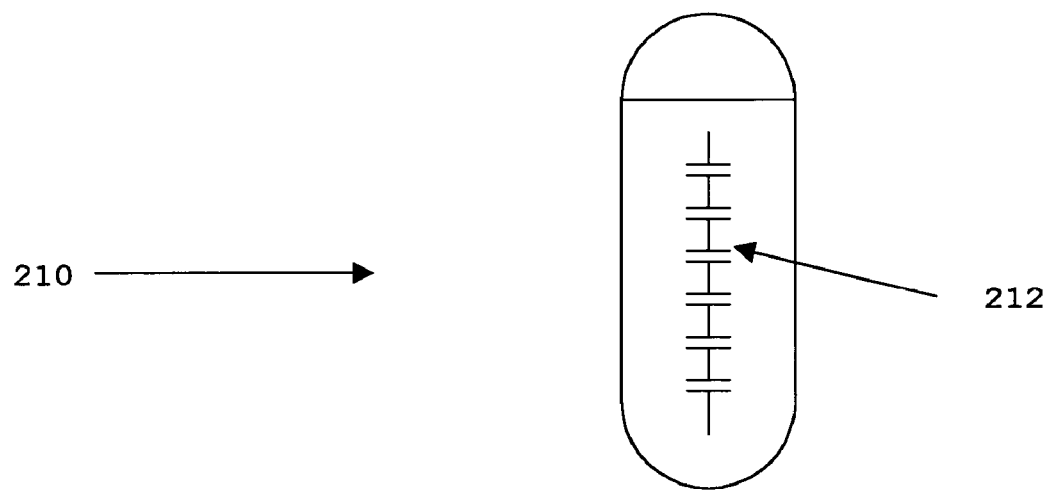

As shown in FIG. 4b, the electromagnetic receiving/signaling system of a vehicle 210 may optionally be composed of a magnetic dipole element 212. In this case, vehicle 210 is powered by an electromagnetic field imposed on the vehicle from the extracorporeal device.

Figure 4C:
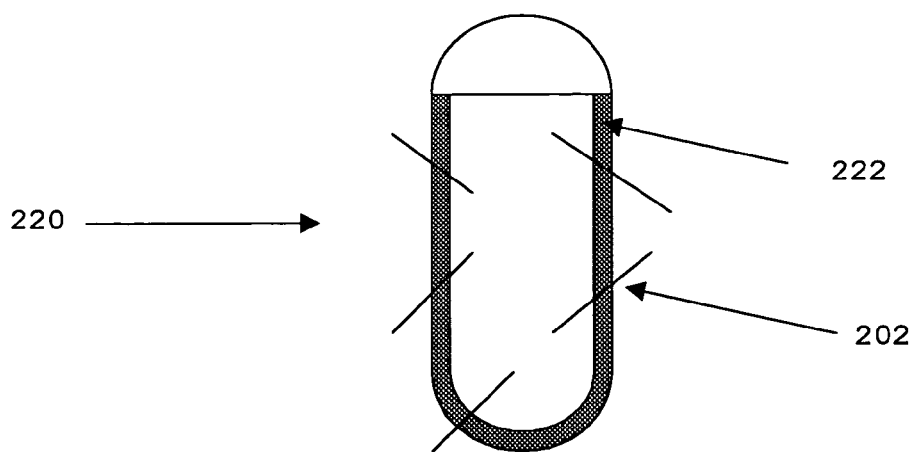

As shown in FIG. 4c, a vehicle 220 may optionally feature a magnetic element 222 which is implemented as a partial or full covering of the exterior of vehicle 220, or even as a partial or full exterior structure for vehicle 220. The degree of the magnetic field which is generated or which is capable of being generated by magnetic element 222 may optionally and preferably be varied in a plurality of different portions of vehicle 220. Each portion may optionally have a different direction of magnetization in order to optimize the control of the movement of vehicle 220.

Figure 4D:
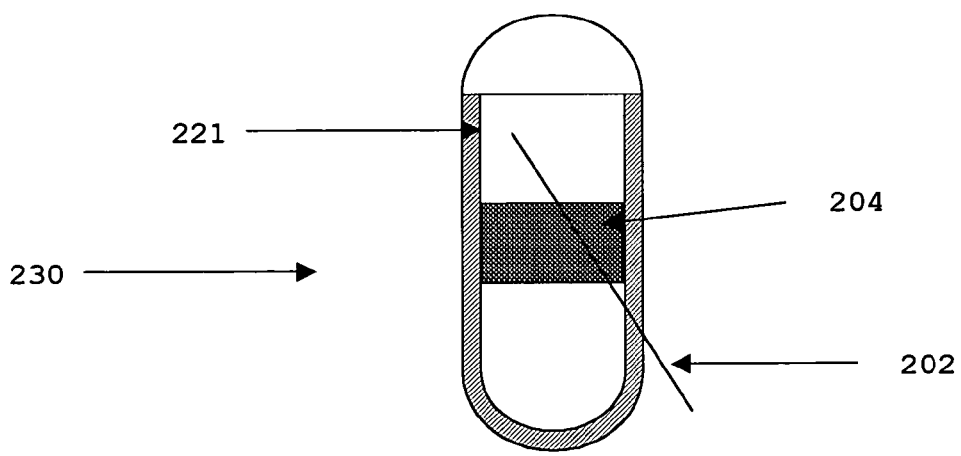

Similarly, for FIG. 4d, a vehicle 230 may optionally feature a partial or full exterior structure 221 made from bonded material, optionally and more preferably with inserted magnet 204, again optionally in the form of a ring or disk, which again is more preferably permanently installed.

Figure 4E:
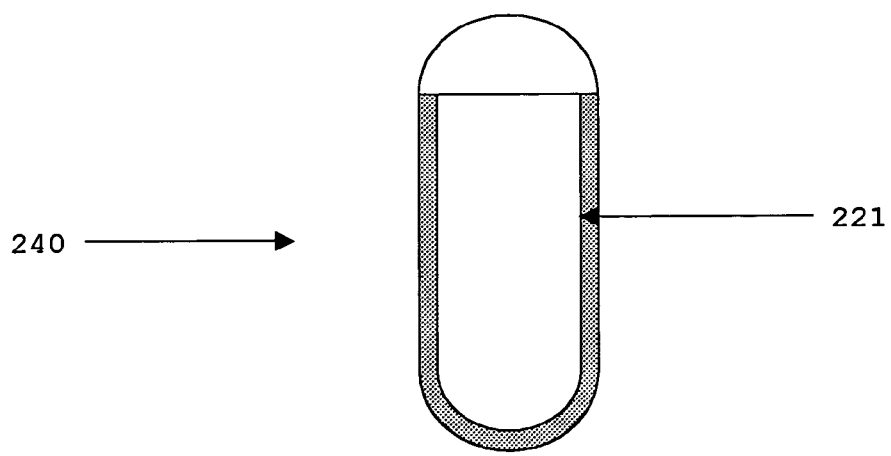

In FIG. 4e, a vehicle 240 is shown with partial or full exterior structure 221 made from bonded material optionally as the sole magnetic element. For either implementation, the bond can optionally be made of dissolvable or non-dissolvable material, and can also optionally partially fill the interior volume of the vehicle.

Figure 4F:
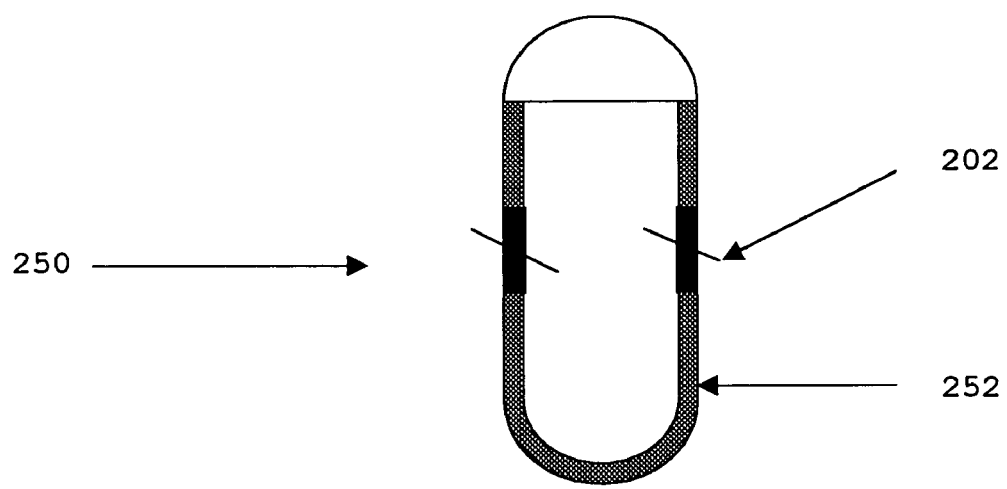
Figure 4G:
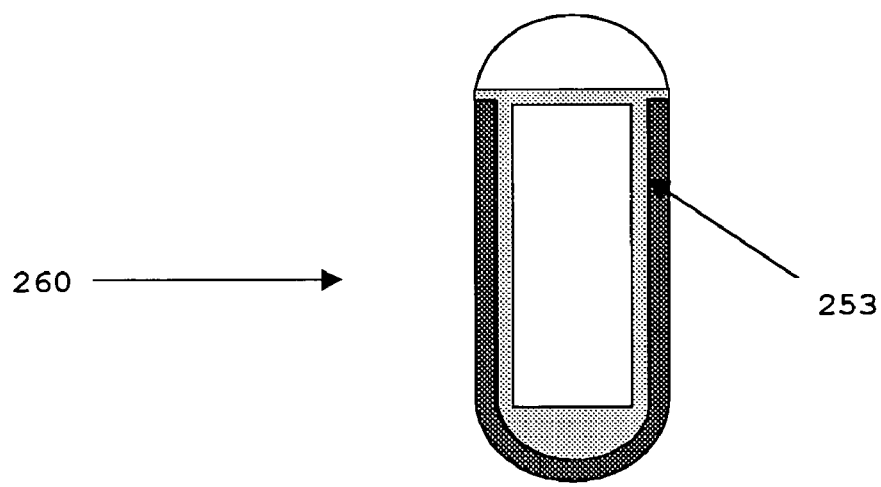

In FIG. 4f, a vehicle 250 is shown with a partial or full exterior structure 252 made from a permanently magnetic or ferromagnetic material. FIG. 4g shows a vehicle 260 with a partial or full exterior structure 253 made from a ferromagnetic material.

Reference is now made to FIG. 5 which describes an exemplary system 50 according to the present invention for controlling and maneuvering the vehicle in the subject's colon. As previously noted, although the following description is directed toward the use of the system of the present invention in the GI tract, this is for the purposes of illustration only and is not intended to be limiting in any way, as the present invention is suitable for use in any bodily cavity, space, vessel, organ or other non-solid section of the body.

Vehicle 51 can be maneuvered within colon 54, and can optionally and preferably be focused on a particular field of view 52. Vehicle 51 is preferably guided by one, and more preferably a plurality of external guidance elements 53 as shown. Each external guidance element 53 could optionally be a coil, reed switch, or Hall effect probe, for example. If a plurality of external guidance elements 53 is used, then vehicle 51 can more easily be located. The plurality of external guidance elements 53 is preferably distributed about the body of the patient (not shown) and then calibrated. The location of external guidance elements 53 and their number depends at least partially upon the accuracy of management of vehicle 51 that is desired and the activity to be performed.

Reference is now made to FIG. 6 which illustrates the detection and motion control systems combined in a single component 60. The field generator units and detector units are contained in one element 61, such that the magnetic field is both produced and detected by element 61. The field generator units can optionally operate on the principle of magnetic flux or electromagnetic field production. The field generating/detector units (elements 61) are preferably distributed on a flexible material 65 and are more preferably connected via power and information buses 62 to a computer control unit 64. Flexible material 65 may optionally be in the form of a blanket or sheet which can be wrapped around at least a portion of the patient.

Figure 7:
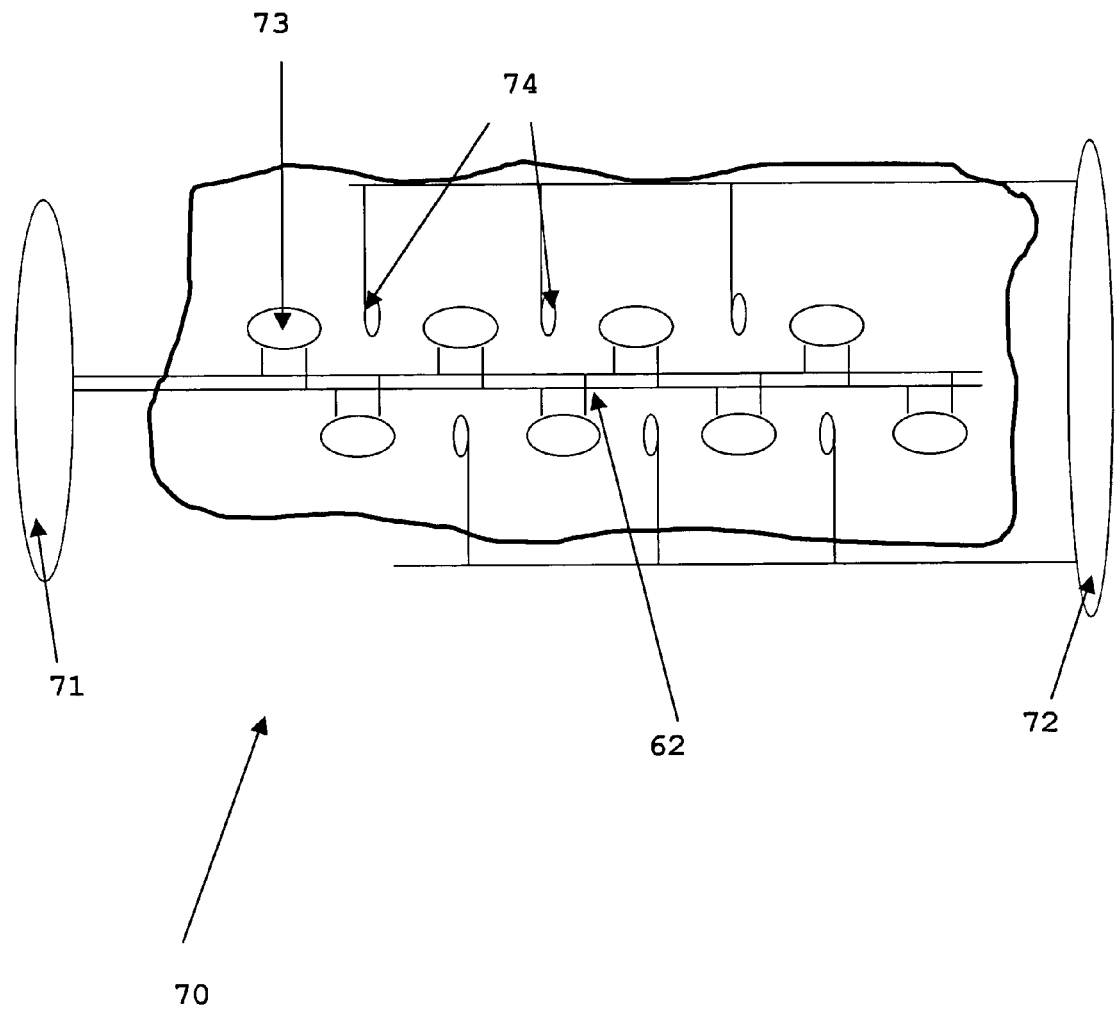
FIG. 7 is a schematic diagram for depicting the detection and motion control subsystems as separate elements distributed on a flexible material, while the detection and motion control subsystems are preferably connected to separate computerized control units.

Reference is now made to FIG. 7 which depicts a different configuration for the detection and motion control subsystems as a separated system 70, such that the magnetic field is generated and detected by different components of system 70. A field generation subsystem computer control unit 71 and a detecting subsystem computer control unit 72 are located in different locations in system 70. As in the combined system depicted in FIG. 6, a field generating element 73 can optionally operate on the principle of production of a magnetic flux or electromagnetic field. Field generating element 73 and a detecting element 74, of which a plurality of each such element are shown for the purposes of description only, are connected to their respective computer control units by power and information buses 62. This implementation is preferred to avoid cross-talk between the generation and detection of the magnetic field, and may also optionally provide greater sensitivity.

Figure 8:
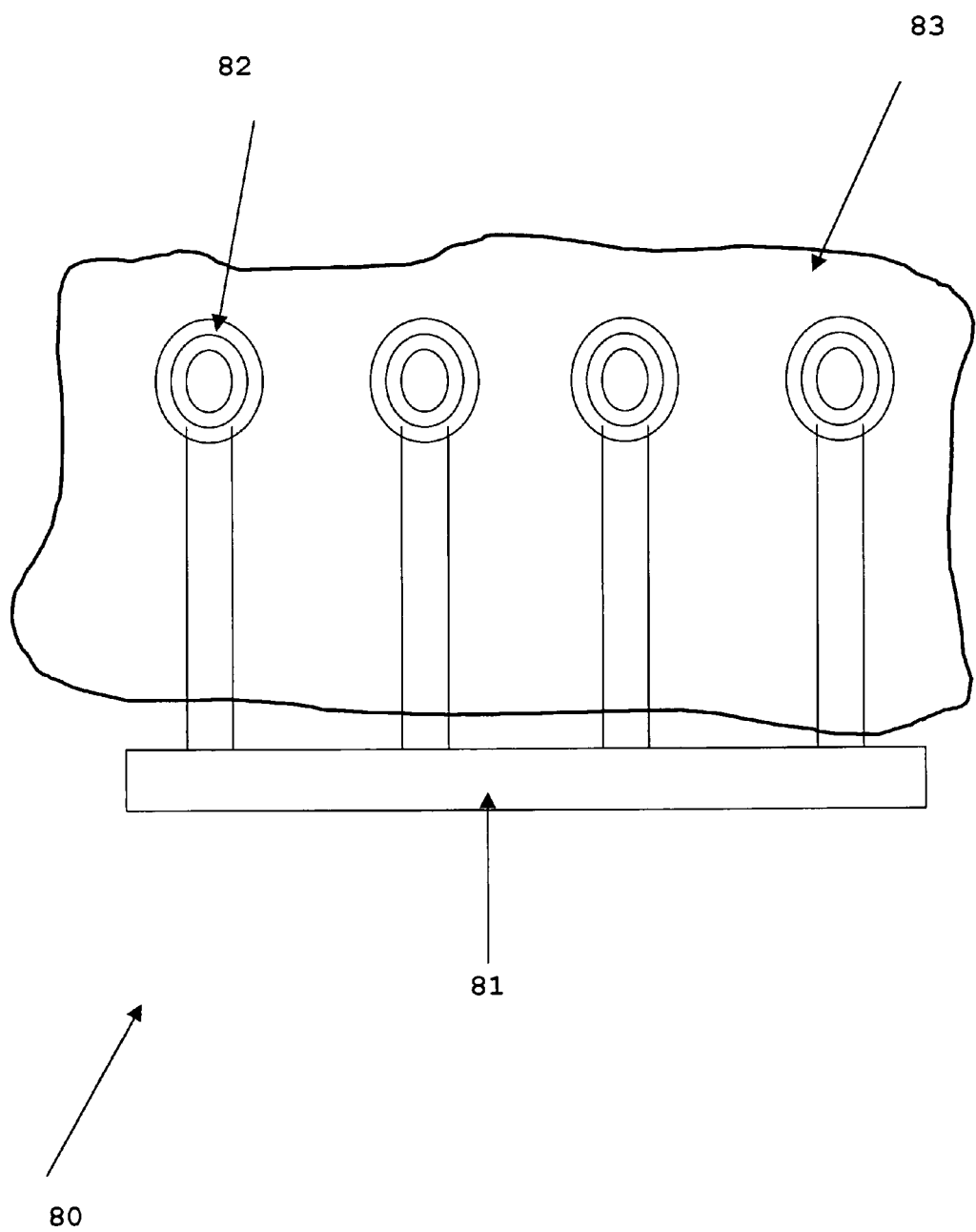
FIG. 8 is a schematic diagram for depicting a system for detecting the vehicle inside the body via Hall effect probes or pressure detectors.

Reference is now made to FIG. 8 which illustrates a prototype detector unit 80. One or more measuring devices 81 are connected to one or more types of field detectors 82. These detectors may include Hall effect probes, pressure detectors, devices for measuring Doppler effects or devices for measuring laser Doppler effects. Measuring device(s) 81 are preferably connected to a switching or indicating device (not shown). The switching or indicating device may optionally be composed of one or more devices such as an individual reed switch or arrays of reed switches, flip switch, electromagnetic, electronic optical or mechanical flag type indicator, LED or memory device which can respond to a signal above or below preset thresholds to locate the vehicle, activate a function or turn off a certain function of the vehicle. Measuring devices 81 and field detectors 82 are preferably attached to a flexible sheet 83, for being wrapped around at least a portion of the patient for example. Flexible sheet 83 may also optionally be implemented as a belt and/or as a rigged board of less flexible material for holding these components.

Figure 9:
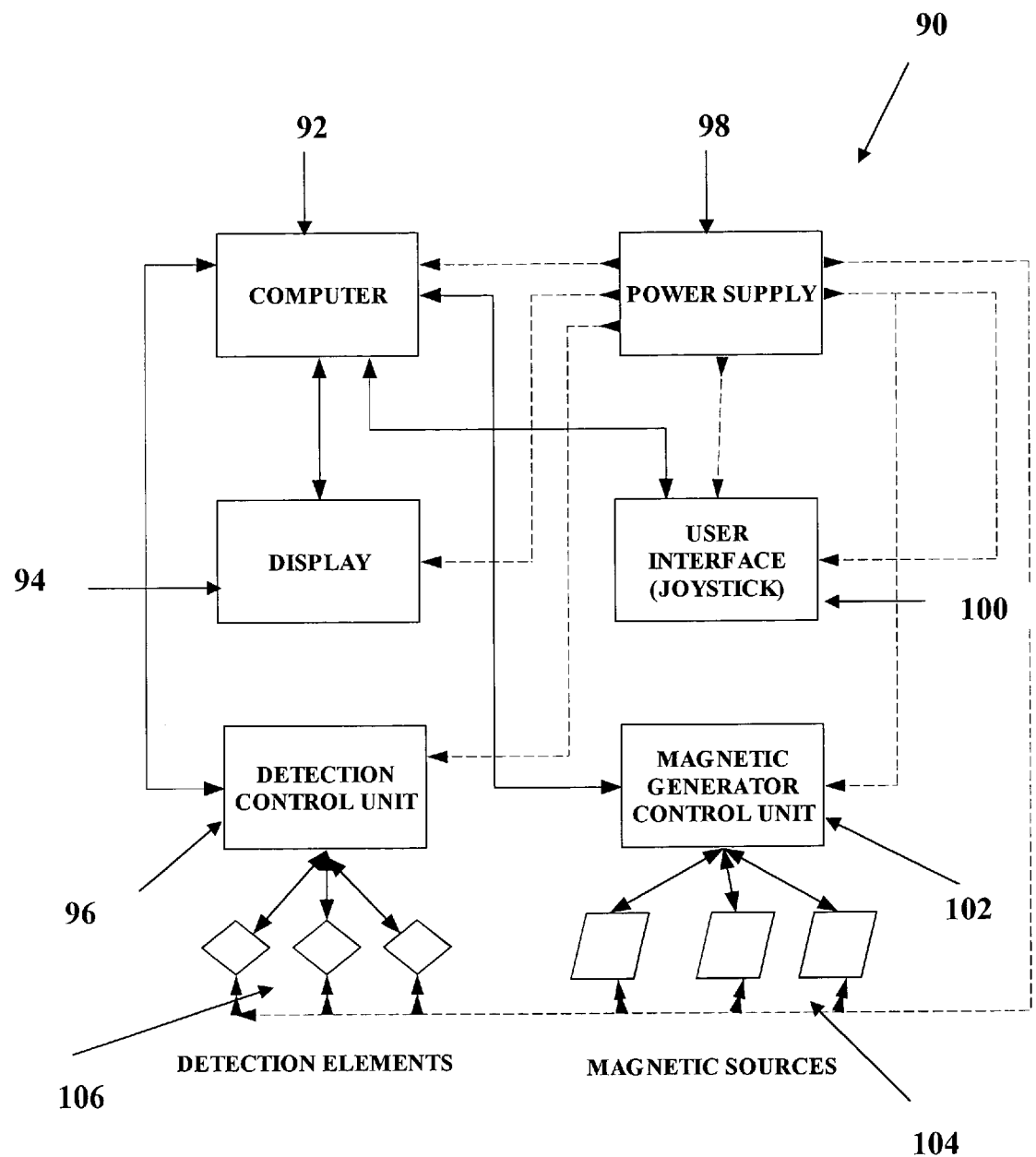
FIG. 9 is a block diagram outlining the interactions of various parts of the extracorporeal generator and detector units.

Reference is now made to FIG. 9, which depicts a block diagram outlining the interactions of various parts of the extracorporeal generator and detector units in an exemplary system 90 according to the present invention. A computer 92 preferably features a display 94 for displaying information to the user about the operation of system 90, more preferably as a graphical user interface (GUI). The user is preferably able to send one or more commands to computer 92 for controlling the behavior of system 90 through a user interface 100, which is optionally and more preferably implemented as a joystick.

A detection control unit 96 preferably receives one or more commands from computer 92 for controlling one or more detection elements 106. Each detection element 106 is preferably capable of detecting a magnetic field, and may optionally be implemented as previously described. Detection control unit 96 optionally and more preferably sends data to computer 92 concerning signals and/or data received from detection element 106.

A magnetic generator control unit 102 is also preferably in communication with computer 92 and also preferably receives one or more commands from computer 92 for controlling the function of one or more magnetic sources 104. Magnetic sources 104 include a magnet and may optionally be implemented as previously described, for example as one material and/or component, or a plurality of materials and/or components.

A power supply 98 optionally supplies power to computer 92, detection control unit 96 and magnetic generator control unit 102, and may optionally also supply power to one or both of detection elements 106 or magnetic sources 104. Power supply 98 may optionally be implemented as a plurality of such power supplies (not shown).

Figure 10:
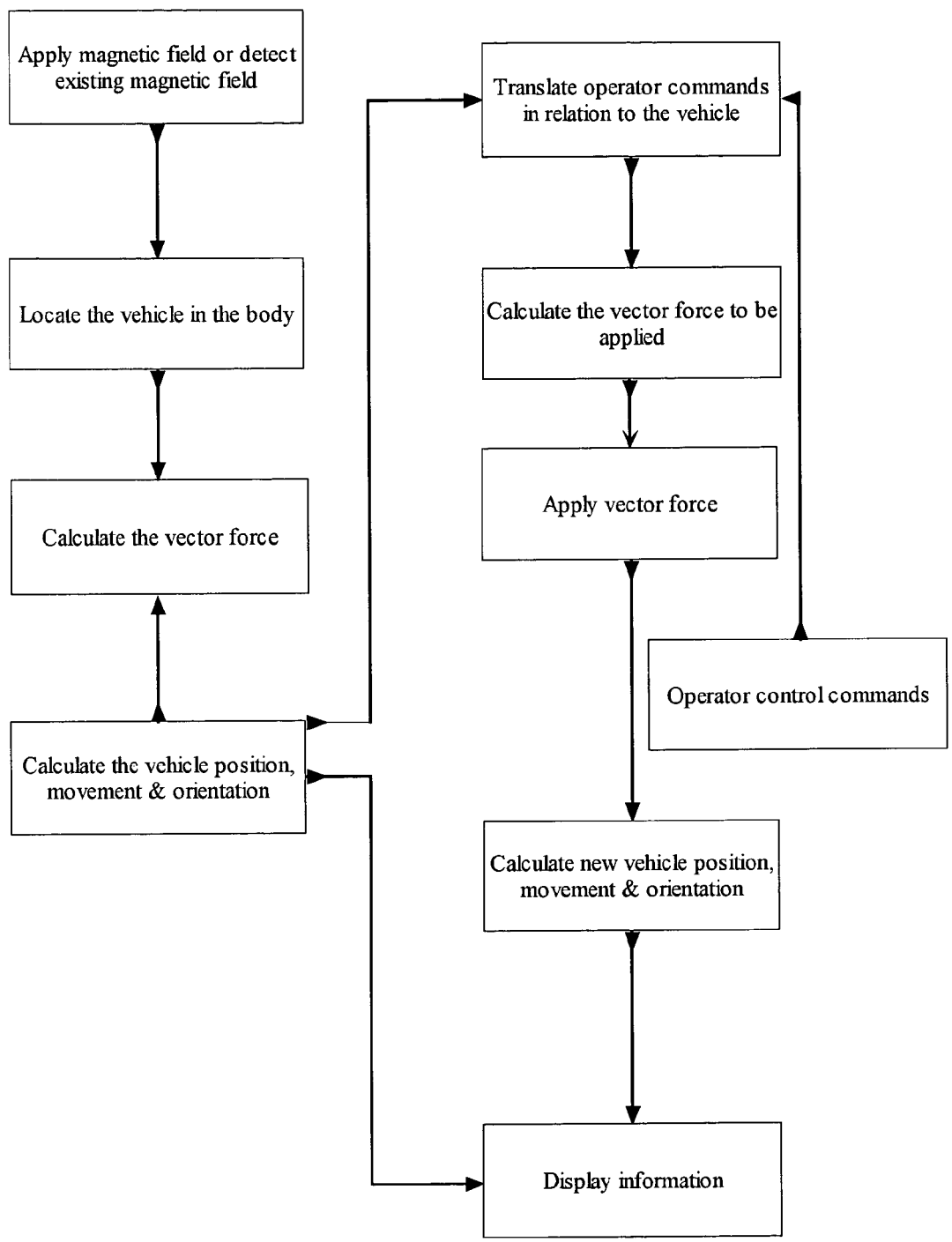
FIG. 10 is a flow chart of the steps involved in measuring and calculating the magnetic field vector of the vehicle and subsequently activating the vehicle.

Reference is now made to FIG. 10 which illustrates a flow chart of the stages involved in measuring and calculating the magnetic field vector of the vehicle and subsequently activating the vehicle. Application of the magnetic field is performed by the generator unit and detection of the signals emitted from the vehicle is performed by the detection unit. The calculations are performed by the computer, which preferably has sufficient power to integrate many complex signals simultaneously.

First, the magnetic field is applied and/or an existing magnetic field is detected. Next, the detector units in the extracorporeal device preferably detect magnetic signals from the vehicle to locate the vehicle. As shown, after the vehicle has been located in the body, next the vector force is calculated for the magnetic field vectors of the vehicle. After performing a best fit calculation, the x, y, z, $m_x$, $m_y$, $m_z$ parameters are estimated (see previous equations for a description). After checking the consistency of the calculation, the current is measured and the force $F_m$ is then calculated. Next, from these calculations, one or more of the vehicle position, movement and orientation are preferably determined.

If one or more operator control commands are received, for example from a human operator, then the operator commands are preferably translated in relation to the location of the vehicle, and more specifically are translated in relation to the magnetic field of the vehicle.

Next, the vector force to be applied to perform the operator command is calculated and the force is then applied. Next, at least one of a new vehicle position, movement and orientation is preferably determined. This information is preferably then displayed to the operator.

Figure 11:
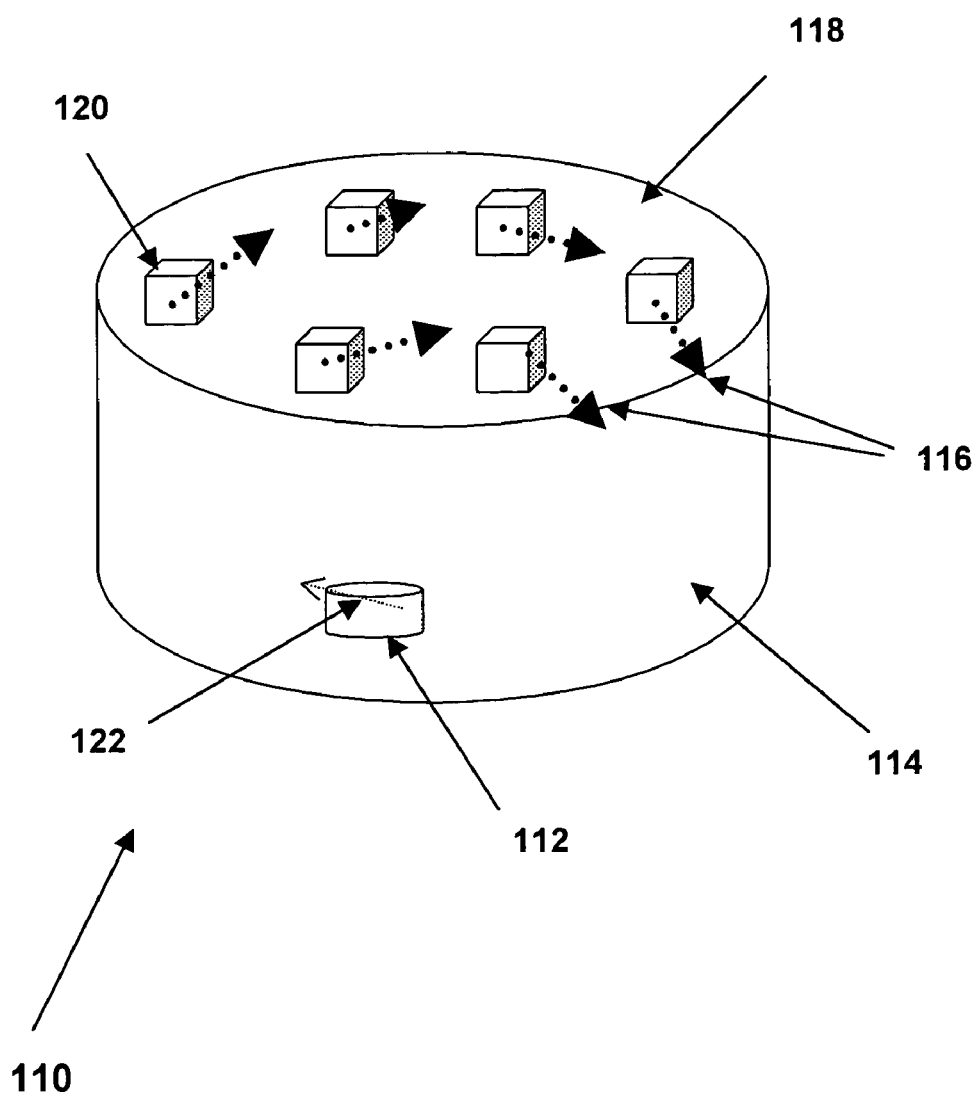
FIG. 11 is a schematic diagram of the calculation of the vector between the detecting element and the vehicle.

Reference is now made to FIG. 11 which provides a schematic description 110 of the calculation of the vector between a plurality of extracorporeal detecting elements 120 and a vehicle 112. In this diagram, vehicle 112 is situated in a body lumen or cavity 114. The vehicle's magnetization vector 122 is detected by detector elements 120 through the skin 118 via interactions with the detector units' magnetic field vectors 116. These signals are preferably processed according to the procedure outlined in FIG. 10.

Having now generally described the invention, the same will be more readily understood through reference to the following examples, which are provided by way of illustration and are not intended to be limiting of the present invention.

EXAMPLES

Example 1

Gastrointestinal (GI) Use of the Invention

The present invention is conceived as being a viable alternative to endoscopy, especially in diagnostic or therapeutic procedures in the esophagus, stomach, small intestine, large intestine and rectum. The invention allows the medical personnel to directly observe the epithelial lining of the GI tract and to carry out medical procedures such as tissue sample collection for histological examination, liquid sampling for microscopic examination and culturing and small surgical procedures such as removal of suspicious polyps in the large intestine. These procedures can be carried out with less danger to the patient since no physical connection between the vehicle and the extracorporeal navigating device is necessary. The invention is useful for carrying out the above functions in the diagnosis of or as part of the treatment of malignant, nonmalignant, infectious, and genetic diseases as well as birth or developmental defects.

Example 2

Application of the Invention in the Bronchus

The present invention is conceived as being a viable alternative to bronchoscopy. The invention allows the medical personnel to directly observe the epithelial lining of the bronchi and to carry out medical procedures such as tissue sample collection for histological examination, liquid sampling for microscopic examination and culturing and small surgical procedures. These procedures can be carried out with less discomfort and danger to the patient since no physical connection between the vehicle and the extracorporeal navigating device is necessary. The invention is useful for carrying out the above functions in the diagnosis of or as part of the treatment of malignant, nonmalignant, infectious, and genetic diseases as well as birth or developmental defects.

Example 3

Applications of the Invention in the Abdomen

The present invention is conceived as being an additional tool used in laparoscopy or as a viable alternative to laparoscopy. As mentioned in the previous examples, the vehicle, under the control of the extracorporeal navigating device, can perform small surgical procedures. The invention could therefore be launched from a laparoscopic instrument into the abdomen to perform a certain task or could actually be used in place of the laparoscope in certain indications such as the destruction of kidney stones, gallstones, or other pathological crystalline deposits in other organs. Alternatively, the invention could be used for directly observing organs and tissues in the abdominal space and for carrying out medical procedures such as tissue sample collection for histological examination, liquid sampling for microscopic examination and culturing and surgical procedures, as part of the diagnosis or treatment of malignant, nonmalignant, infectious, and genetic diseases as well as birth or developmental defects.

Example 4

Drug Delivery

The present invention is conceived as being a means for directly controlling and optimizing drug delivery to a specified tissue or organ. The pharmaceutical compound can be encapsulated into liposomes or any other suitable form for delivery to the target organ and magnetic particles can be impregnated into the structure of the delivery device in such a way so that the extracorporeal navigating system can concentrate them into the desired location. Alternatively and preferably, magnetic particles can be coated with the therapeutic or structures containing the therapeutic such as liposomes or microspheres and these can serve as the drug delivery vehicle. Such a drug delivery system could be administered orally, intravenously or parenterally depending on the indication as determined by those skilled in the art.

Example 5

Force Amplifying Using a Coil Matrix

As stated, (see equation 1 above) the force on the axis decreases rapidly with the distance. The greater the distance from the body the lower the force is.

Figure 12:
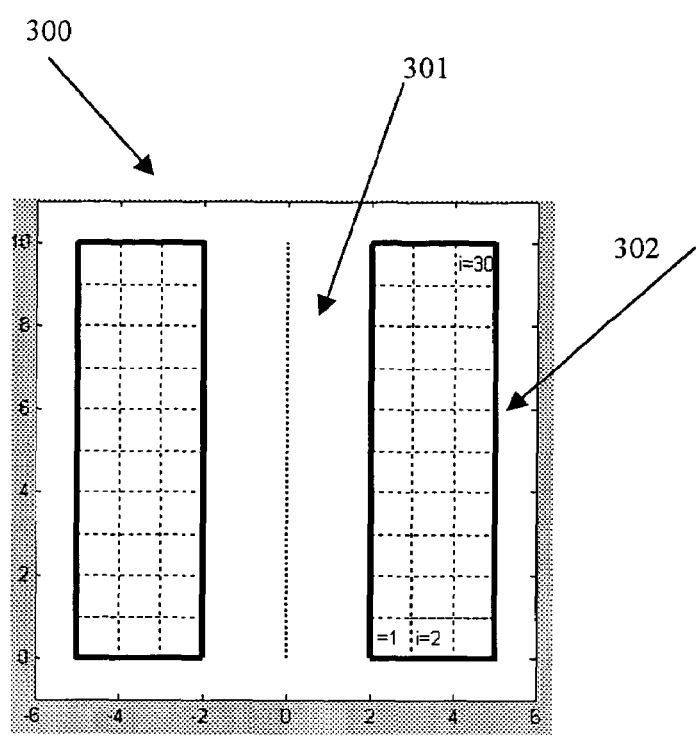
FIG. 12 is an outline picture of a solenoid for amplifying the force in the system.

Reference is now made to FIG. 12, which describes two solenoids 300 each with maximal radius of 5 mm and length of 10 mm. Each solenoid is built of 30 turns 302 of cross-section 1 mm$^2$. The dotted line 301 is the axis of symmetry. The maximal radius of the coil determines the pixel size of the vehicle. A distance smaller than the radius of a coil cannot be specified, due to space discretization, and therefore the coil radius cannot be larger than 5 mm for a pixel size of 1 cm.

From equation 1 above, for a coil of radius 5 mm, which has current density of less than 5 ampere/mm$^2$, it can be seen that the effective region of the force is practically limited to a height of 4 mm from the base of the coil.

Due to the limitation on the current density as described above, the small size of the coil results in a limitation on the force that the coil can impose on the vehicle. A small imposed force requires the vehicle to be in short distance from the coil matrix. One needs a force amplifier to enlarge the force a small coil can create.

An optional method of force amplification is to use a matrix of coils, which can be activated and deactivated and thus used in order to move a permanent magnet. The permanent magnet moves to the center of the switched on coils, and creates an equivalent effective high current density at this point. The equivalent effective high current density then amplifies the force created by the coils on the vehicle.

An amplified force created on the vehicle can control its movement. The vehicle will move to the geometric center of the activated coils. In order to know the vehicle position with a good resolution, the coils composing the matrix must be of small dimension, namely having a size in the order of millimeters, and not centimeters. Therefore, the discretization size determines the coil size. The size of the coils also determines the "pixel" size of the vehicle. Optionally and preferably, the coil size is less than about 5 mm, such that the pixel size is also preferably less than about 5 mm.

Example 6

Force Amplification Using a Matrix of Permanent Cylindrical Magnets

As mentioned above in example 5, the present invention may have an extracorporeal electromagnet of several coils creating a magnetic field, which may cause a problem due to low current density in these coils.

A possible way of amplifying the force on this electromagnetic field is by using a matrix of cylindrical permanent magnets arranged on a grid. Cylindrical magnets are chosen as they are the most efficient way to utilize the space, but the magnet can optionally be ring shaped, a polygon or a polygonal ring; a magnet having any such suitable shape and geometry is herein termed an "annular magnet". The cylindrical magnets are magnetized in the axial direction, and this is due to the fact that an axial magnet is like a solenoid (as mentioned in hereinabove), which produces the same field in all directions. The formula for calculating the force created by the cylindrical magnets is the same as equation 1, except that the sum is only on the cylindrical surface.

One important concept for such a system is space discretization, which is achieved by dividing the surface into regions of the magnetic field. A region having magnetic field in the one direction, when all its nearest neighboring pixels have a magnetic field in the opposite direction defines a surface pixel. The change of directions is achieved by placing magnets of opposite direction in neighboring regions, such that each magnet has a magnetization opposite to the magnetization of its nearest neighbors (non diagonal neighbors).

Figure 13:
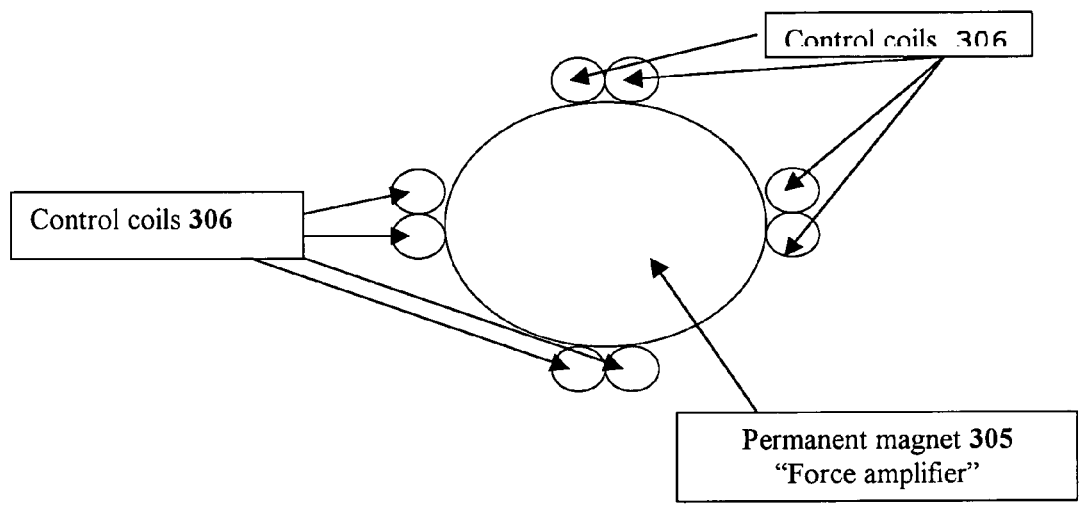
FIG. 13 depicts the layout of the control coils around the permanent magnet for the system, when amplifying its force.
Figure 14:
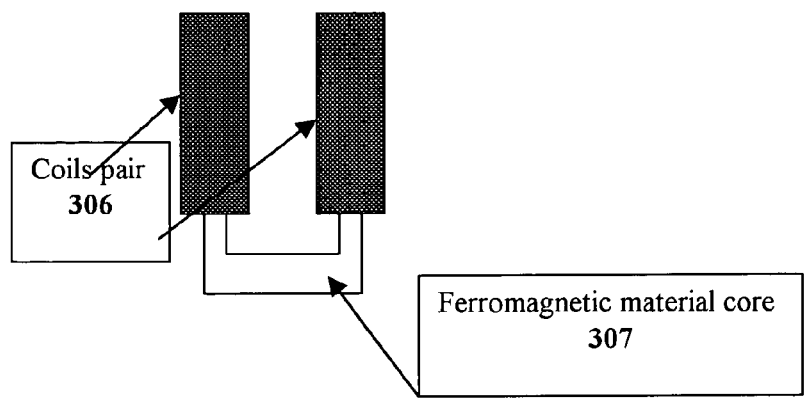
FIG. 14 is a closeup of the two paired coils, mounted on ferromagnetic material, which are connected to the permanent magnet at different angles.

Referring now to FIG. 13, on the movable permanent magnet 305, several coils 306 are attached. A pair of coils is placed at every 90° around the permanent magnet 305, as displayed in the figure. The reason for this choice of angle is once again because of space utilization. The angle also determines the direction, and therefore it is most efficient to create a grid that has two orthogonal directions (90°), but it is possible to create a grid in which the two directions are not orthogonal (for example having an angle of 65.4°). If the direction chosen is not orthogonal, the coils will have the same angle between them, yet the force will be smaller. The two coils that create a pair of coils as depicted in FIG. 13, are wound in opposite directions (one coil is wound clockwise and the other coil is wound counterclockwise). One coil is below the magnet and has a positive magnetic field (N), and the second coil is below the magnet and has a negative magnetic field (S). Having the two coils wound in opposite directions causes each of the two coils to be affected also by the force of its paired coil. Since the force of the two coils is in the same direction, the total force in the system will be maximized. Moreover, looking now at FIG. 14, as the two coils 306 are mounted on ferromagnetic material 307, and the ferromagnetic connection between them increases the force created in the system.

Example 7

Breaking the Symmetry and Hall Effect Probes

Figure 15:
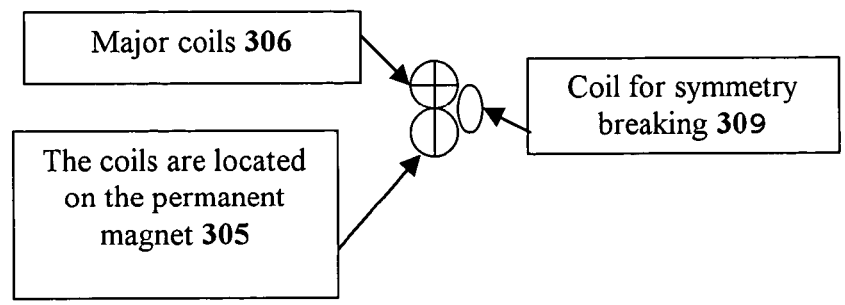
FIG. 15 depicts the system when a $3^{rd}$ coil is added to each pair to break the symmetry of paired coils connected to the permanent magnet.

When using the matrix of cylindrical magnets as described above in example 6, the movement of the vehicle in the body lumen is caused by a change in the direction of the current in the coils. As depicted in FIG. 15, to assist the change of direction, it is possible to add a third coil 309 to each pair of coils 306 on the permanent magnet 305, to break their symmetry.

Using the extra coil to break the symmetry, it is possible to give preference to one of the pairs that are alien in 180°, and by that create a preferred direction of movement. The movement in the system stops when all the coils are in the center of the pixel, meaning that every coil center is directly on the axis of the cylindrical magnet above it.

In the above situation the force is axial, and therefore changing the current in the coils would once again cause an axial force and there would be no movement. The extra coil mentioned above is added in order for movement to start. This coil is preferably not placed below the magnet's center; therefore it will experience non-axial force, which will create a movement. Once the system moves, the force on the major coils will no longer be axial, and the symmetry breaking coils can be shut down. In this stage, the inertia serves as a tool for breaking the symmetry between the coils.

In the preferred embodiment of the present invention in which several Hall-effect probes are added, the movement of the force amplifier relative to the matrix of cylindrical magnets is monitored thereby. The Hall-effect probe monitors field changes hence can be used to trigger a change of the current in the coils when they pass from pixel to pixel. Additionally, the Hall-effect probe can be used for counting the number of pixels that the vehicle moves. Knowing the size of a region with a magnetic field in one direction, the number of changes of field direction is sufficient to determine the distance. More specifically, the distance equals the number of field changes multiplied by the length of each pixel. The direction in which the vehicle is moving can also be determined according to the current direction in the coils.

In order to create movement, the current direction in the coils pair changes every time the coils move a distance similar to the distance between two magnets in the matrix, just as it is done in linear motors. Once the coils enter a new pixel, they have a current in the direction which creates an attraction force to the center of the pixel, and once they cross the pixel center the current direction changes and the coils repulse from the pixel center and are attracted by the next pixel center, because in the next pixel the magnetic field is in the opposite direction to the pixel the coil are currently in. This continues until the coils reach the goal destination, where the current stops changing, and the coils stop at the center of the pixel where the force is axial. The Hall-effect probe, measures the field changes, and is used for changing the current in the coils.

Having now fully described certain preferred embodiments of this invention, it will be appreciated by those skilled in the art that the same can be performed within a wide range of equivalent parameters, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art. The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A system for managing an in vivo vehicle in a subject, comprising:
   a. a magnet being physically associated with the vehicle;
   b. an extracorporeal magnetic source for producing a magnetic field for being applied to said magnet, said extracorporeal magnetic source being located outside of the subject;
   c. a detector for detecting a magnetic field from said magnet, said detector being located outside of the subject; and
   d. a control module for receiving a magnetic field measurement from said detector and for managing the vehicle according to said magnetic field measurement;
   wherein said detector and said extracorporeal magnetic source are assembled on a flexible sheet that is adapted to be attached to the subject.

2. The system of claim 1, wherein managing the vehicle includes at least one of maneuvering, rotating, locating, mobilizing, controlling, monitoring and activating at least one vehicle function.

3. The system of claim 1, wherein application of said magnetic field comprises application of a gradient of said magnetic field.

4. The system of claim 1, wherein said magnet includes an electromagnet.

5. The system of claim 4, wherein said extracorporeal magnetic source features a plurality of coils to measure at least one of a distance and a location of the vehicle, by measuring at least one time dependent change of said magnetic field resulting from movement of the vehicle.

6. The system of claim 1, wherein said magnet includes a soft magnet.

7. The system of claim 1, wherein said magnet includes a hard magnet.

8. The system of claim 1, wherein said magnet includes a ferromagnetic material.

9. The system of claim 1, wherein said magnet is a permanent magnet, comprising at least one material for producing a permanent magnet having permanent magnetization.

10. The system of claim 1, wherein said magnet is a permanent magnet made from at least one material being magnetized in a magnetic field.

11. The system of claim 10, wherein said permanent magnet is part of an outer surface of the vehicle.

12. The system of claim 11, wherein an entire exterior surface of the vehicle is said permanent magnet.

13. The system of claim 10, further comprising a connecting element for connecting said permanent magnet to the vehicle.

14. The system of claim 13, wherein said connecting element is used as an antenna to send and receive signals to and from the vehicle.

15. The system of claim 1, wherein the force and directional vectors between said magnet and said extracorporeal magnetic source are used to calculate a location of the vehicle.

16. The system of claim 1, wherein the vehicle's path inside the body is preplanned.

17. The system of claim 16, wherein the vehicle's preplanned path relies on the anatomical structure of the examined organ or examined area.

18. The system of claim 17, wherein the vehicle's path inside the body is controlled at least partially according to information received about a location of the vehicle.

19. The system of claim 18, wherein said information is received from at least one of a separate imaging system or diagnostic system.

20. The system of claim 19, wherein the vehicle's path inside the body is controlled at least partially according to information received directly from the vehicle.

21. The system of claim 1, further comprising a receiver for receiving at least one of a data input or a command, said receiving being located in the vehicle.

22. The system of claim 1, wherein activation of a function of the vehicle is triggered by a timer.

23. The system of claim 1, wherein activation of a function of the vehicle is triggered by a distance counter.

24. The system of claim 23, wherein said activation of said function of the vehicle is triggered by distance measurement according to the Doppler principal.

25. The system of claim 23, wherein said activation of said function of the vehicle is triggered by distance measurement performed by a laser Doppler.

26. The system of claim 1, wherein activation of a function of the vehicle is triggered, per time frame and/or anatomic position, by an element outside the subject.

27. The system of claim 1, wherein activation of a function of the vehicle is triggered by signals originating from at least one of said extracorporeal magnetic source and said magnetic field from the vehicle.

28. The system of claim 1, wherein activation of said function of the vehicle is triggered by a change of pH at the area where the vehicle is located.

29. The system of claim 1, wherein activation of said function of the vehicle is triggered by a change of at least one electrolyte concentration at the location where the vehicle is located.

30. The system of claim 1, wherein activation of said function of the vehicle is triggered by a change of pressure on the vehicle.

31. The system of claim 1, wherein the vehicle contains elements that perform histological tests.

32. The system of claim 1, wherein the vehicle contains an element for performing a local surgical procedure.

33. The system of claim 1, wherein a single Hall probe or an array of Hall probes measures the vehicle's location inside the subject.

34. The system of claim 1, wherein a pressure applied by or on the vehicle is measured by a pressure-measuring element, and a change in said magnetic force caused by said pressure is sensed by said detector.

35. The system of claim 34, wherein said pressure is also used to calculate an inclination angle of the vehicle.

36. The system of claim 1, wherein a single reed switch or an array of reed switches is used to determine a location of the vehicle.

37. The system of claim 1, wherein said detector indicates when the vehicle passes a predetermined location.

38. The system of claim 37, wherein said detector comprises at least one a reed switch for determining when the vehicle has passed said predetermined location.

39. The system of claim 37, wherein said detector comprises an array of reed switches for determining when the vehicle has passed said predetermined location.

40. The system of claim 37, wherein an indicator is used to indicate when the vehicle passes said predetermined location.

41. The system of claim 40, wherein said indicator is selected from the group consisting of an electromagnetic, electronic, optical and mechanical flip switch.

42. The system of claim 40, wherein said indicator is selected from the group consisting of an electromagnetic, electronic, optical arid mechanical flag type indicator.

43. The system of claim 40, wherein said indicator is a LED or lamp.

44. The system of claim 1, wherein said magnet is at least partially composed of a powder of magnetic material.

45. The system of claim 1, wherein said vehicle further comprises one or more of an imaging element, a functioning element, a power source and a transmitting element.

46. A system for managing an in vivo vehicle in a subject, wherein managing includes at least determining a location of the vehicle in the subject, the system comprising:
  a. a magnet being physically associated with the vehicle;
  b. an extracorporeal magnetic source for producing a magnetic field for being applied to said magnet, said extracorporeal magnetic source being located outside of the subject; and
  c. a detector for detecting a magnetic field from said magnet, said detector being located outside of the subject, such that a location of the vehicle is determined according to said magnetic field measurement;
  wherein said detector indicates when the vehicle passes a predetermined location and comprises an array of reed switches for determining when the vehicle has passed said predetermined location.

47. A system for managing an in vivo vehicle in a subject, comprising:
  a. a magnet being physically associated with the vehicle;
  b. an extracorporeal magnetic source for producing a magnetic field for being applied to said magnet, said extracorporeal magnetic source being located outside of the subject;
  c. a detector for detecting a magnetic field from said magnet, said detector being located outside of the subject; and
  d. a control module for receiving a magnetic field measurement from said detector and for managing the vehicle according to said magnetic field measurement, wherein said managing is performed by modulating at least one of a strength and a direction of said magnetic field from said magnet;
  wherein said magnet is a permanent magnet made from at least one material being magnetized in a magnetic field, and said system further comprises a connecting element in the form of an antenna to send out and receive signals from the vehicle.

48. The system of claim 47, wherein said control module modulates said magnetic field by inducing a plurality of changes in said magnetic field with specific characteristics over time.

49. The system of claim 48, wherein said extracorporeal magnetic source is an electromagnet and said magnetic field is an electromagnetic field, and said control module causes said extracorporeal magnetic source to produce at least one pulse in said electromagnetic field to induce said changes in said magnetic field.

50. A system for amplifying the force in an electromagnetic field used for controlling and managing an in vivo vehicle in a subject, comprising:
  a. A permanent magnet being physically associated with the vehicle;
  b. An extracorporeal magnetic source for producing a magnetic field for being applied to said magnet, said extracorporeal magnetic source being located outside of the subject, being comprised of a matrix of coils;
  c. A detector for detecting a magnetic field from said magnet, said detector being located outside of the subject; and
  d. A control module for receiving a magnetic field measurement from said detector and for managing the vehicle according to said magnetic field measurement;
  wherein a pressure applied by or on the vehicle is measured by a pressure-measuring element, and a change in said magnetic force caused by said pressure is sensed by said detector.

51. The system of claim 50, wherein said coils in said matrix are capable of being activated and deactivated.

52. The system of claim 50, wherein said coils in said matrix are of small dimensions, such that the pixel size and the coil size determined according to a discretization size.

53. The system of claim 50, wherein controlling and managing the vehicle includes moving the vehicle.

54. A system for amplifying the force in an alectromagnetic fiels used for controlling and managing an in vivo vehicle in a subject, comprising:
  a. A magnetic being physically associated with the vehicle;
  b. An extracorporeal magnetic source for producing a magnetic field for being applied to said magnetic, said extracorporeal magnetic source being located outside of the subjects, being comprised of a matrix of annular permanent magnets arranged on a grid;
  c. A detector for detecting for detecting a magnetic field from said magnet, said detector being located outside of the subject; and
  d. A control module for receiving a magnetic field measurement from said detector and for managing the vehicle according to said magnetic field measurement.

55. The system of claim 54, wherein said annular magnets comprise a ring shaped magnet.

56. The system of claim 55, wherein each said annular magnet has a magnetization in the opposite direction to that of its nearest neighbors.

57. The system of claim 54, wherein said annular magnets comprise a ring shaped magnet.

58. The system of claim 54, wherein said annular magnets comprise a polygonal magnet.

59. The system of claim 54, wherein said annular magnets comprise a polygonal ring magnet.

60. The system of claim 54 wherein said annular magnets are magnetized in the axial direction.

61. The system of claim 54, wherein the surface of said electromagnetic field is divided into regions.

62. The system of claim 54, wherein said annular magnet is attached to several coils.

63. The system of claim 62, wherein said coils are in pairs.

64. The system of claim 63, wherein said pairs of said coils are wound in opposite directions.

65. The system of claim 63, wherein said pairs of said coils are located at 90 degree angles around said annular magnet.

66. The system of claim 63, wherein each said pair of said coils is attached to a third coil, in order to break the symmetry in the system.

67. The system of claim 66, wherein said added coil is magnetized by a non axial force.

68. The system of claim 54, wherein said system further comprises several Hall effect probes.

69. The system of claim 68, wherein said Hall effect probes monitor the movement of said force amplifier with relation to said matrix of annular magnets.

70. The system of claim 68, wherein said Hall effect probes are used to change the current in said coils.

71. The system of claim 68, wherein said Hall effect probes measure the changes in the electromagnetic field.

72. The system of claim 68, wherein said Hall effect probes are used to count the number of pixels having field changes along the grid of permanent magnets, for determining the distance the vehicle moved and the current position of the vehicle.

* * * * *